United States Patent [19]

Homann

[11] Patent Number: 4,808,747
[45] Date of Patent: Feb. 28, 1989

[54] PROCESS FOR PRODUCING ALKYLIDENE COMPOUNDS AND ARYLIDENE COMPOUNDS

[75] Inventor: Walter K. Homann, Dülmen, Fed. Rep. of Germany

[73] Assignee: Hüls AG, Marl, Fed. Rep. of Germany

[21] Appl. No.: 711,712

[22] Filed: Mar. 14, 1985

[30] Foreign Application Priority Data

Jun. 23, 1984 [DE] Fed. Rep. of Germany ....... 3423249

[51] Int. Cl.$^4$ ........................................... C07C 120/00
[52] U.S. Cl. ..................................... 558/374; 560/82; 560/127; 560/203; 562/489; 562/509; 562/595; 568/927; 568/942; 568/943
[58] Field of Search ............ 260/465.8 R, 464, 465 D, 260/465.4; 560/203, 82; 562/595; 558/374

[56] References Cited

PUBLICATIONS

Schmall et al., C.A., 84, 105052f, (1976).
Fujioka et al., C.A., 88, 191363v, (1978).
Fuhrhop et al., C.A., 86, 29784v, (1977).
Texier-Boulvet et al., C.A., 98, 178718b, (1983).
Attanasi et al., C.A., 100, 191500d, (1984).
Cabello et al., C.A., 102, 23817k, (1985).
Cabello et al., C.A., 102, 131661p, (1985).
Patai (Editor), "The Chemistry of the Carbonyl Group", (1966), pp. 593 & 594, Interscience, N.Y.
Organic Reactions, vol. 15, (1967), Chapter 2, by Jones, pp. 204–268 and 381–599.

Primary Examiner—Joseph Paul Brust
Attorney, Agent, or Firm—Gilbert L. Wells

[57] ABSTRACT

Alkylidene compounds and arylidene compounds are prepared by reacting the corresponding CH-acidic compounds with carbonyl compounds in the presence of a catalyst comprising a metal compound of a metal of Groups IIA, IIIA, IVA, IB, IIB, VIB, VIIB, or VIIIB of the periodic table of elements. The rate of reaction is increased by adding 1 to 40% water referred to the weight of catalyst used.

8 Claims, No Drawings

PROCESS FOR PRODUCING ALKYLIDENE COMPOUNDS AND ARYLIDENE COMPOUNDS

BACKGROUND OF THE INVENTION

The field of the invention is alkylidene compounds and arylidene compounds and the present invention is particularly concerned with the production thereof.

Alkylidene and arylidene compounds are prepared by the Knoevenagel reaction by condensing a carbonyl component with CH-acidic methylene compounds, for instance acetaldehyde with malonic-acid diethylester. Illustratively, amines acting as catalysts are piperidine or alanine in the presence of acetic acid:

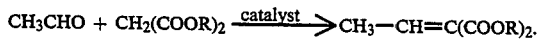

The state of the art of Knoevenagel condensation reactions is disclosed in ORGANIC REACTIONS, Vol. 15, pp. 204–597, as published by John Wiley and Sons, Inc. (1957), the disclosure of which is incorporated herein by reference. Pages 274–581 of this reference include a tabular survey of the known Knoevenagal condensation reactions.

A further compound obtained in the reaction of acetaldehyde with malonic acid diethylester is the dicarboxylated product as disclosed by Henecka in Houben-Weyl, Vol. 8, pp. 365–502 (1952).

To displace the equilibrium, it is recommended that reaction water be entrained out of circulation using such means as benzene, toluene or chloroform. Substantially basic catalysts such as sodium or potassium acetate cause disproportionate by-product formation due to telomerization as disclosed in the *Journal of Organic Chemistry*, Vol. 38, p. 1512 (1973).

By CH-acidic compound is meant: Aldehydes, ketones, acids, esters, nitriles and nitrocompounds with at least one hydrogen atom in α-position to the functional group.

SUMMARY OF THE INVENTION

Having in mind the limitations of the prior art, there is significance in a process not requiring on the one hand the use of special extractants and avoiding, on the other hand, disproportionate formation of by-products.

According to the present invention, the process for producing alkylidene compounds and arylidene compounds by reacting the corresponding CH-acidic compounds with carbonyl compounds by carrying out the reaction in the presence of a metal compound of a metal of Groups IIA, IIIA, IVA, IB, IIB, VIB, VIIB, VIIIB, of the periodic table of elements or a mixture of metal compounds from these Groups A and B.

The disproportionate formation of by-products incurred in the presence of sodium or potassium acetate does not take place with the metal compounds of the present invention.

Referred to the CH-acidic compound, a catalyst concentration between 0.001 and 2 mole percent, preferably between 0.01 and 0.7 mole percent, is used. Lower catalytic concentrations result in disadvantageous space-time yields, and higher concentrations cause problems in reprocessing.

Contrary to expectation based upon the prior art, the reaction is favorably affected in the presence of about 1 to 40% water, preferably 10 to 30%, referred to weight of the metal compound. The reaction rate is increased.

The conversion takes place at low temperatures, for instance about 10° to 150° C. The preferred operational temperatures are between 40° and 100° C. The reaction, however, is also carried out at higher and at lower temperatures. At low temperatures it, however, proceeds more slowly while at high temperatures a significant increase in the formation of by-products is noted.

As a rule, atmospheric pressure is used, though higher and reduced pressure are also practical. To carry out the reaction, the carbonyl component, as a rule, is introduced first with the catalyst and the CH-acidic compound is then metered into the temperature-controlled medium. When all of the reaction components are inserted together to be then temperature-controlled, negative effects regarding the selectivity of the reaction process are to be expected.

DESCRIPTION OF THE PREFERRED EMBODIMENTS

Suitable useful CH-acidic compounds are malonic acid, malonic acid ester, malonic acid dinitrile, cyanacetic acid, cyanacetic ester, and aliphatic nitro compounds such as nitromethane.

When the reaction is completed, the crude product is isolated by single vacuum fractionation. Water of reaction, including any catalyst residues contained therein, can be removed beforehand. When product isolation is not required, the concentration of metal compounds can be reduced as necessary to the desired residue content by conventional processes such as washing or by using ion exchangers.

Suitable carbonyl compounds are aldehydes or ketones such as acetaldehyde, propionaldehyde, butyraldehyde, valeraldehyde, 2-methylvaleraldehyde, capronaldehyde, laurylaldehyde, benzaldehyde, 2-phenylpropanal, 3-phenylpropanal or acetone, methylethylketone, methylbutylketone, cyclohexanone and 4-tert.-butyl-cyclohexanone.

Suitable catalysts are the metal compounds of a metal of Groups IIA, IIIA, IVA, IB, IIB, VIB, VIIB, and VIIIB of the periodic table of elements. Specific examples of these metal compounds used as catalysts include acylates such as calcium acetate, calcium propionate, lead acetate, lead propionate, aluminum acetate, aluminum propionate, copper acetate, copper propionate, zinc acetate, zinc propionate, cadmium acetate, cadmium propionate, chromium acetate, chromium propionate, manganese acetate, manganese propionate, iron acetate, iron propionate, cobalt acetate, cobalt propionate, nickel acetate, nickel propionate, and mixtures thereof.

Preferably zinc compounds are used such as the zinc acylates, in particular zinc acetate, zinc propionate, and mixtures thereof. Also, cobalt compounds, cadmium compounds, and mixtures thereof are used, preferably the acylates. High conversion rates with good yields are obtained when these catalysts are used.

No significant deactivation can be noted when the catalytic system is used again.

From about 1 to 40% water, preferably 10 to 30% referred to the weight of catalyst used, is added to advantageously affect the rate of reaction. This can take place both by means of freely available water and by means of the water of crystallization. Again, it is possible to use higher water proportions. However, no further positive effects of signigicant nature take place.

Examples of the alkylidene compounds and arylidene compounds produced by the present invention include, but are not limited to, ethylidene cyanacetic ester, propylidene malonic acid dinitrile, nitropentene, pentylidene malonic acid ester, hexylidene malonic acid, dodecylidene malonic acid ester, benzylidene malonic acid ester, 2-phenylpropylidene malonic acid ester, 3-phenylpropylidene malonic acid ester, isopropylidene malonic acid dinitrile, 2-methylpropylidene cyanacetic ester, 2-methylbutylidene malonic acid dinitrile, cyclohexylidene cyanacetic ester, 4-tert.-butylcyclohexylidene cyanacetic ester, butylidene malonic acid ester, butylidene malonic acid ester, and butylidene malonic acid ester.

The following specific examples further illustrate the embodiments of the present invention.

EXAMPLES

In each of the examples tabulated below, 1 mole of the carbonyl component and 0.02 mole of the catalyst are heated to the temperature of reaction in a three-neck flask with attached condenser and the reaction is carried out within 8 hours with one mole of the CH-acidic compound. Reaction water is removed upon completion of the reaction and the reaction solution is reprocessed in vacuum by distillation.

In the table, the conversion and the yield refer to the CH-acidic component.

| | Carbonyl Compound | CH-acidic Component | Reaction Product | Catalyst | Temp. of Reaction °C. | Conversion % | Yield % |
|---|---|---|---|---|---|---|---|
| 1 | Acetaldehyde | cyanacetic ester | ethylidene cyanacetic ester | Calcium-acetate | | 90 | 68 |
| 2 | Propionaldehyde | malonic-acid dinitrile | propylidene malonic-acid dinitrile | Zinc propionate | 60 | 96 | 92 |
| 3 | Butyraldehyde | Nitromethane | Nitropentene | Zinc oxide | 80 | 76 | 22 |
| 4 | Valeraldehyde | malonic-acid ester | pentylidene malonic-acid ester | Zinc acetate | 60 | 89 | 91 |
| 5 | Capronaldehyde | malonic acid | hexylidene malonic acid | Zinc chloride | 80 | 88 | 41 |
| 6 | Laurylaldehyde | malonic acid ester | dodecylidene malonic acid ester | Iron hydroxy acetate | 80 | 45 | 28 |
| 7 | Benzaldehyde | malonic acid ester | benzylidene malonic acid ester | Cobalt acetate | 100 | 92 | 32 |
| 8 | 2-Phenylpropanal | malonic acid ester | 2-phenylpropylidene malonic acid ester | Nickel acetate | 100 | 83 | 94 |
| 9 | 3-Phenylpropanal | malonic acid ester | 3-phenylpropylidene malonic acid ester | Manganese acetate | 100 | 79 | 89 |
| 10 | Acetone | malonic acid dinitrile | isopropylidene malonic acid dinitrile | Cadmium acetate | 40 | 100 | 68 |
| 11 | Methylethylketone | cyanacetic ester | 2-methylpropylidene cyanacetic ester | Zinc acetate | 60 | 92 | 78 |
| 12 | Methylbutylketone | malonic acid dinitrile | 2-methylbutylidene malonic-acid dinitrile | Lead acetate | 80 | 78 | 64 |
| 13 | Cyclohexanone | cyanacetic ester | Cyclohexylidene cyanacetic ester | Cobalt acetate | 100 | 75 | 94 |
| 14 | 4-tert.-butylcyclohexanone | cyanacetic ester | 4-tert.-butylcyclohexylidene cyanacetic ester | Zinc acetate | 100 | 72 | 93 |
| 15 | Butyraldehyde | malonic acid ester | Butylidene malonic acid ester | Copper acetate | 70 | 46 | 85 |
| 16 | Butyraldehyde | malonic acid ester | Butylidene malonic acid ester | Chromium acetate | 70 | 38 | 52 |
| 17 | Butylaldehyde | malonic acid ester | Butylidene malonic acid ester | Aluminum acetate | 70 | 26 | 54 |

Corresponding to the above disclosed examples, butyl aldehyde is made to react with malonic acid ester under the catalytic influence of zinc acetate. The table below shows the effect of various water concentrations (referred to the catalyst) on the rate of reaction. The reference point is a product-content in the reaction mixture of equal concentration.

| | Water Content % | Reaction-Temperature °C. | Duration or Reaction hours |
|---|---|---|---|
| 18 | <1 | 60 | 24 |
| 19 | 18 | 60 | 7 |
| 20 | 30 | 60 | 9 |
| 21 | 70 | 60 | 19 |

What I claim is:

1. In the process for producing alkylidene compounds and arylidene compounds by reacting the corresponding CH-acidic compounds with carbonyl compounds, the improvement comprising:
carrying out the reaction at a temperature of between about 10° to 150° C. in the presence of a catalytic amount of a metal compound at a catalyst concentration between about 0.001 and 1 mole percent based on said CH-acidic compound and in the presence of about 1 to 40% water referred to the weight of said metal compound wherein said CH-acidic compounds are selected from the group consisting of malonic acid, malonic acid ester, malonic acid dinitrile, cyanacetic acid, cyanacetic ester and nitromethane, said carbonyl compounds are selected from the group consisting of acetaldehyde, propionaldehyde, butyraldehyde, valeraldehyde, 2-methylvaleraldehyde, capronaldehyde, laurylaldehyde, benzaldehyde, 2-phenylpropanal, 3-phenylpropanal, acetone, methylethylketone, methylbutylketone, cyclohexanone and 4-tert.-butyl-cyclohexanone and said metal compound is selected from the group consisting of calcium acetate, calcium propionate, lead acetate, lead propionate, aluminum acetate, aluminum propionate, copper acetate, copper propionate, zinc acetate, zinc propionate, cadmium acetate, cadmium propionate, chromium acetate, chromium propionate, manganese acetate, manganese propionate, iron acetate, iron propionate, cobalt acetate, cobalt propionate, nickel acetate, nickel propionate and mixtures thereof.

2. The process of claim 1, wherein said catalyst concentration is between 0.01 and 0.7 mole percent.

3. The process of claim 2, wherein the reaction is carried out in the presence of 10 to 30% water referred to the weight of metal compound.

4. The process of claim 1, wherein said metal compound is zinc acetate.

5. The process of claim 1, wherein said metal compound is zinc propionate.

6. The process of claim 4, wherein the water content is 10 to 20% by weight.

7. The process of claim 5, wherein the water content is 10 to 20% by weight.

8. The process of claim 1, wherein the reaction is carried out at a temperature between about 40° to 100° C.

* * * * *